(12) United States Patent
Peng et al.

(10) Patent No.: US 9,927,404 B2
(45) Date of Patent: Mar. 27, 2018

(54) PHASED ARRAY BILLET DATA EVALUATION SOFTWARE

(71) Applicant: UNITED TECHNOLOGIES CORPORATION, Farmington, CT (US)

(72) Inventors: Wenji Peng, Glastonbury, CT (US); Jeffrey A Umbach, Palm Beach Garden, FL (US); Kevin D Smith, Glastonbury, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 238 days.

(21) Appl. No.: 14/761,151

(22) PCT Filed: Dec. 16, 2013

(86) PCT No.: PCT/US2013/075256
§ 371 (c)(1),
(2) Date: Jul. 15, 2015

(87) PCT Pub. No.: WO2014/143258
PCT Pub. Date: Sep. 18, 2014

(65) Prior Publication Data
US 2015/0355145 A1    Dec. 10, 2015

Related U.S. Application Data

(60) Provisional application No. 61/776,224, filed on Mar. 11, 2013.

(51) Int. Cl.
*G01N 29/26* (2006.01)
*G01N 29/06* (2006.01)

(52) U.S. Cl.
CPC ....... *G01N 29/262* (2013.01); *G01N 29/0645* (2013.01); *G01N 2291/0234* (2013.01);
(Continued)

(58) Field of Classification Search
CPC .................. G01N 29/262; G01N 29/0645
See application file for complete search history.

(56) References Cited

U.S. PATENT DOCUMENTS 4,127,033 A * 11/1978 Warren .................. G01N 29/07
                                                    73/622
5,533,401 A    7/1996 Gilmore
(Continued)

FOREIGN PATENT DOCUMENTS

WO    WO 2009-017892 A1    2/2009

OTHER PUBLICATIONS

International Search Report Application No. PCT/US2013/075256 dated Apr. 15, 2014.

*Primary Examiner* — Ryan Walsh
(74) *Attorney, Agent, or Firm* — Cantor Colburn LLP

(57) ABSTRACT

A computer-implemented method for evaluating echo signals obtained from a phased array experiment on a billet is disclosed. The computer-implemented method may comprise collecting the echo signals from a pulser/receiver unit, correlating the echo signals with a position on a longitudinal axis and a circumferential angle of the billet, computing an amplitude for each of the echo signals, displaying the amplitudes as indications in a c-scan data plot at a computer display unit, and determining the signal-to-noise ratios of indications located in a region-of-interest box relative to noise in surrounding boxes in the c-scan data plot. The computer-implemented method may further comprise classifying each indication as rejectable, reportable, or insignificant based on its amplitude and signal-to-noise ratio. The (Continued)

computer-implemented method may find applications in quality control evaluations in the aircraft industry.

20 Claims, 9 Drawing Sheets

(52) U.S. Cl.
CPC . *G01N 2291/044* (2013.01); *G01N 2291/106* (2013.01); *G01N 2291/2634* (2013.01); *G01N 2291/2694* (2013.01)

(56) References Cited

U.S. PATENT DOCUMENTS

| | | | |
|---|---|---|---|
| 6,220,099 B1* | 4/2001 | Marti | G01N 29/226 |
| | | | 73/633 |
| 6,579,238 B1 | 6/2003 | Simopoulos | |
| 7,237,438 B1* | 7/2007 | Umbach | G01N 29/07 |
| | | | 73/597 |
| 2010/0242613 A1* | 9/2010 | Simard | G01N 29/262 |
| | | | 73/641 |
| 2011/0083512 A1 | 4/2011 | Imbert et al. | |
| 2011/0257903 A1* | 10/2011 | Imbert | G01M 13/045 |
| | | | 702/35 |
| 2012/0048021 A1 | 3/2012 | Ochiai et al. | |
| 2012/0055252 A1 | 3/2012 | Boehm | |

* cited by examiner

| Indication # | Axial Position, inches | Angle, degrees | Amplitude, % | Average Noise | Average Peak Noise | S/N | Status |
|---|---|---|---|---|---|---|---|
| 1 | 27.3 | 80 | 60 | ## | ## | 2.0 | reportable |
| 2 | 48 | 52 | 51 | ## | ## | 1.9 | reportable |
| 3 | 102 | 210 | 45 | ## | ## | 1.7 | reportable |
| 4 | 36 | 312 | 80 | ## | ## | 3.0 | rejectable |
| 5 | 73 | 18 | 75 | ## | ## | 2.9 | rejectable |
| 6 | 115 | 95 | 71 | ## | ## | 2.4 | rejectable |

FIG. 10

| Indication # | Axial Position, inches | Angle, degrees | Amplitude, % | Corrected Amplitude | Average Noise | Average Peak Noise | S/N | Corrected S/N | Status | Corrected Status |
|---|---|---|---|---|---|---|---|---|---|---|
| 1 | 27.3 | 80 | 60 | 70 | ## | ## | 2.0 | 2.2 | reportable | rejectable |
| 2 | 48 | 52 | 51 | — | ## | ## | 1.9 | | reportable | |
| 3 | 102 | 210 | 45 | | ## | ## | 1.7 | | reportable | |
| 4 | 36 | 312 | 80 | | ## | ## | 3.0 | | rejectable | |
| 5 | 73 | 18 | 75 | | ## | ## | 2.9 | | rejectable | |
| 6 | 115 | 95 | 71 | | ## | ## | 2.4 | | rejectable | |

PHASED ARRAY BILLET DATA EVALUATION SOFTWARE

CROSS-REFERENCE TO RELATED APPLICATION

This application is a US National Stage under 35 USC § 371 of International Patent Application No. PCT/US13/75256 filed on Dec. 16, 2013 based on U.S. Provisional Patent Application Ser. No. 61/776,224 filed on Mar. 11, 2013.

FIELD OF DISCLOSURE

The present disclosure generally relates to a computer-implemented method for evaluating and processing non-destructive testing data, and more specifically, relates to a computer-implemented method for evaluating and processing ultrasonic phased-array echo data signals arising from structural defects in billets.

BACKGROUND

The detection of structural flaws in components that are designed for incorporation into larger structures such as machines, buildings, or engines is important for ensuring the quality, safety, and operation of such structures. In particular, the detection of structural flaws in cylindrical titanium billets, which are ultimately incorporated into aircraft engine disks, is an important endeavor in the aerospace industry. For example, structural flaws or defects in billets such as voids, cracks, holes, discontinuities, and inclusions may be detrimental to the operation of aircraft engine disks and the aircraft as a whole if appropriate measures are not taken to remove the flawed region of the billet. Also, in the case of titanium billets, it is necessary to downgrade a heat of material if a hard-alpha inclusion is found so that it is not used as prime rotor material for a jet engine application. In order to address such concerns, non-destructive testing techniques such as ultrasonic testing (UT) have been employed to detect the size and position of structural flaws in billets without affecting the structural integrity of the billet in any way. When flaws are detected above a pre-defined threshold value, the flawed portion of the billet may be excised to ensure that only the highest quality material is incorporated into aircraft engine components.

The UT technique employs a probe carrying a transducer element that sends a high frequency ultrasonic beam through a test material. The transducer element is typically a piezo-electric material that converts electrical pulses into ultrasonic sound waves and vice versa. When the ultrasonic beam comes into contact with a structural defect, ultrasonic waves, referred to as 'echoes', are reflected back to the transducer element. The transducer element subsequently converts any reflected echo signal into electrical signals that are sent to a computer controlled instrument. The computer translates any received electrical signals into a readable data display, known as a c-scan, and reports information relating the size and location of any structural defects to the operator.

A disadvantage of conventional UT employing a single transducer element is apparent during the inspection of cylindrically-shaped billets, however. Billet imperfections, such as circumferential out-of-roundness or bowing, may cause the probe to tilt away from the central axis of the billet, such that portions of the billet center may miss inspection entirely.

The phased array ultrasonic inspection technique is an advanced variation of the conventional UT inspection technique and overcomes some of its inherent limitations. Phased array ultrasonic testing employs an array of multiple transducer elements in a single probe unit. The individual transducer elements in the array can be separately pulsed to transmit ultrasonic waves according to programmed time-delays. The pulsed ultrasonic waves interact constructively or destructively to create a predictable primary wavefront, or ultrasonic beam, that travels through the test material. By the use of focal laws that contain time delays for firing the individual elements of the transducer, it is possible to strategically time the firing of the pulsed ultrasonic waves from the multiple transducer elements in order to shape the beam, steer or sweep the beam through angles, and/or vary the depth of the beam focus through the test material. Software called a focal law calculator establishes the specific time delays for firing each of the transducer elements required to produce the desired angle for beam steering, the desired depth of focus, and/or the desired beam shape for probing the test material.

During phased array inspection, any reflected echo signals arising from structural defects are received by the transducer elements in the array and are converted to electrical signals that are sent to a computer. The computer displays the amplitude of reflected echo signals and reports the position of the defect to the operator. Echo information may be displayed as a c-scan image which provides a two-dimensional representation of the material as a flattened or planar view.

The ability of the phased array technique to permit beam steering or beam sweeping through angles greatly enhances the detection of flaws in cylindrical billets compared with conventional UT, as it ensures that the entire cylindrical volume of interest, including the billet center, is inspected even if the probe is tilted away from the central axis.

One limitation of the ultrasonic testing method for the non-destructive testing of titanium billets is the high number of false detections that can arise from background noise due, in part, to the granular structure of titanium. Furthermore, due to the mechanics of rotating billets weighing thousands of pounds as well as limitations due to finite increments of data collection used during the scan process, it should be assumed that when a flaw is detected it may not have been detected optimally. Therefore, echo signals that fall below a pre-established rejection threshold should be identified for closer evaluation by the inspector performing the ultrasonic test.

A system is needed to evaluate phased array echo data from billets by accounting for background noise in order to improve the reliability of structural defect signals and reduce or eliminate false detections. Moreover, a system is needed to improve the evaluation of echo signals obtained during automated phased array measurements.

SUMMARY OF THE DISCLOSURE

In accordance with one aspect of the present disclosure, a computer-implemented method for evaluating echo signals obtained from a phased array experiment on a billet is disclosed. The method may comprise collecting the echo signals from a pulser/receiver unit, correlating the echo signals with a position on a longitudinal axis and at a circumferential angle of the billet, computing an amplitude for each of the echo signals, displaying the amplitudes as indications in a c-scan data plot at a computer display unit, and determining a signal-to-noise ratio for each indication located in a region-of-interest box relative to surrounding boxes in the c-scan plot. The signal-to-noise ratios may be determined by the equation: signal-to-noise ratio=(A−B)/(C−B), where A may be the amplitude of the indication in the region-of-interest box, B may be the average of the average noise in the surrounding boxes, and C may be the average of the highest signal amplitudes in the surrounding boxes.

In another refinement, determining the signal-to-noise ratio for each indication located in a region-of-interest box may be performed for the entire volume of a first cylindrical zone of the billet.

In another refinement, determining the signal-to-noise ratio for each indication located in a region-of-interest box may be further performed for the entire volume of a second cylindrical zone of the billet.

In another refinement, determining the signal-to-noise ratio for each indication located in the region-of-interest box may be determined relative to eight surrounding boxes.

In another refinement, the computer-implemented method may further comprise classifying each indication as reportable, rejectable, or insignificant based on the signal-to-noise ratio and the amplitude of each indication.

In another refinement, each indication having an amplitude falling within a pre-defined range of signal amplitudes may be classified as reportable.

In another refinement, the pre-defined range of signal amplitudes may be percent amplitudes between about 40% and about 70%.

In another refinement, each indication having an amplitude equal to or above a pre-defined amplitude threshold may be classified as rejectable.

In another refinement, the pre-defined amplitude threshold may be a percent amplitude of about 70%.

In another refinement, each indication having a signal-to-noise ratio above a pre-defined signal-to-noise threshold may be classified as rejectable.

In another refinement, the pre-defined signal-to-noise threshold may be a signal-to-noise ratio of 2.5.

In another refinement, the computer-implemented method may further comprise displaying an output data table at the computer display unit. The output data table may list the amplitudes of reportable and rejectable indications, the position of the reportable and rejectable indications on the longitudinal axis and the circumferential angle of the billet, the signal-to-noise ratios of the reportable and rejectable indications, and the classification of the reportable and rejectable indications as reportable or rejectable.

In another refinement, a reportable indication may notify the operator to manually measure the amplitude of the indication.

In another refinement, the computer-implemented method may further comprise receiving operator input of the manually measured amplitude of the reportable indication.

In another refinement, the computer-implemented method may further comprise re-classifying the manually measured amplitude as reportable, rejectable, or insignificant.

In another refinement, the computer-implemented method may be performed for the entire volume of the first cylindrical zone and the second cylindrical zone.

In accordance with another aspect of the present disclosure, a computer-implemented method for evaluating echo signals obtained from a phased array experiment on a billet is disclosed. The phased array experiment may be performed by transmitting an ultrasonic beam through the billet and the ultrasonic beam may be swept through an angle. The computer-implemented method may comprise collecting the echo signals from a pulser/receiver unit, correlating the echo signals with a position on a longitudinal axis and a circumferential angle of the billet, and computing an amplitude for each of the echo signals. The computer-implemented method may further comprise displaying the amplitudes as indications in a raw c-scan data plot at a computer display unit. The raw c-scan data plot may have a series of aligned low-resolution incremental c-scan plots and each incremental c-scan plot may correspond to an angular increment of the sweeping angle. The computer-implemented method may further comprise merging the incremental c-scan plots to provide a high-resolution c-scan plot and displaying the high-resolution c-scan plot at the computer display unit.

In another refinement, the computer-implemented method may further comprise determining a signal-to-noise ratio for each indication located in a region-of-interest box relative to surrounding boxes in the high-resolution c-scan plot. Each signal-to-noise ratio may be determined by the equation: signal-to-noise ratio=(A−B)/(C−B), where A may be the amplitude of the indication in the region-of-interest box, B may be the average of the average noise in the surrounding boxes, and C may be the average of the highest signal amplitudes in the surrounding boxes.

In another refinement, determining the signal-to-noise ratios for each indication located in a region-of-interest box may be performed for the entire volume of a first cylindrical zone of the billet.

In another refinement, determining the signal-to-noise ratio for each indication located in a region-of-interest box may be performed for the entire volume of a second cylindrical zone of the billet.

In another refinement, the computer-implemented method may further comprise classifying each indication as reportable, rejectable, or insignificant based on the signal-to-noise ratio and the amplitude of each indication.

In another refinement, each indication having an amplitude falling within a pre-defined range of signal amplitudes may be classified as reportable.

In another refinement, each indication having an amplitude greater than or equal to a pre-defined amplitude threshold may be classified as rejectable.

In another refinement, each indication having a signal-to-noise ratio greater than or equal to a pre-defined signal-to-noise threshold may be classified as rejectable.

In accordance with another aspect of the present disclosure, a billet inspection system comprising an immersion tank adapted to hold a billet, a probe unit to direct an ultrasonic beam toward the billet, and a pulser/receiver unit in communication with the probe unit and a computer central processing unit is disclosed. The computer central processing unit may be configured to perform computer executable instructions for evaluating echo signals obtained from a phased array experiment on the billet. The computer executable instructions may comprise instructions for collecting the echo signals from the pulser/receiver unit, correlating the echo signals with a position on a longitudinal axis and a circumferential angle of the billet, computing an amplitude for each of the echo signals, and displaying the amplitudes as indications in a c-scan data plot at a computer display unit. The computer executable instructions may further comprise instructions for determining a signal-to-noise ratio for each indication located in a region-of-interest box relative to surrounding boxes in the c-scan data plot. The signal-to-noise ratios may be determined by the equation: signal-to-noise ratio=(A−B)/(C−B), where A may be the amplitude of the indication in the region-of-interest box, B may be the average of the average noise in the surrounding boxes, and C may be the average of the highest signal amplitudes in the surrounding boxes.

BRIEF DESCRIPTION OF THE DRAWINGS

FIG. 10 is a representative output data table in accordance with the present disclosure.

FIG. 11 is a representative output data spreadsheet displayed at a user interface provided by a data analysis program in accordance with the present invention.

It should be understood that the drawings are not necessarily drawn to scale and that the disclosed embodiments are sometimes illustrated diagrammatically and in partial views. In certain instances, details which are not necessary for an understanding of this disclosure or which render other details difficult to perceive may have been omitted. It should be understood, of course, that this disclosure is not limited to the particular embodiments disclosed herein.

DETAILED DESCRIPTION

Figure 1:
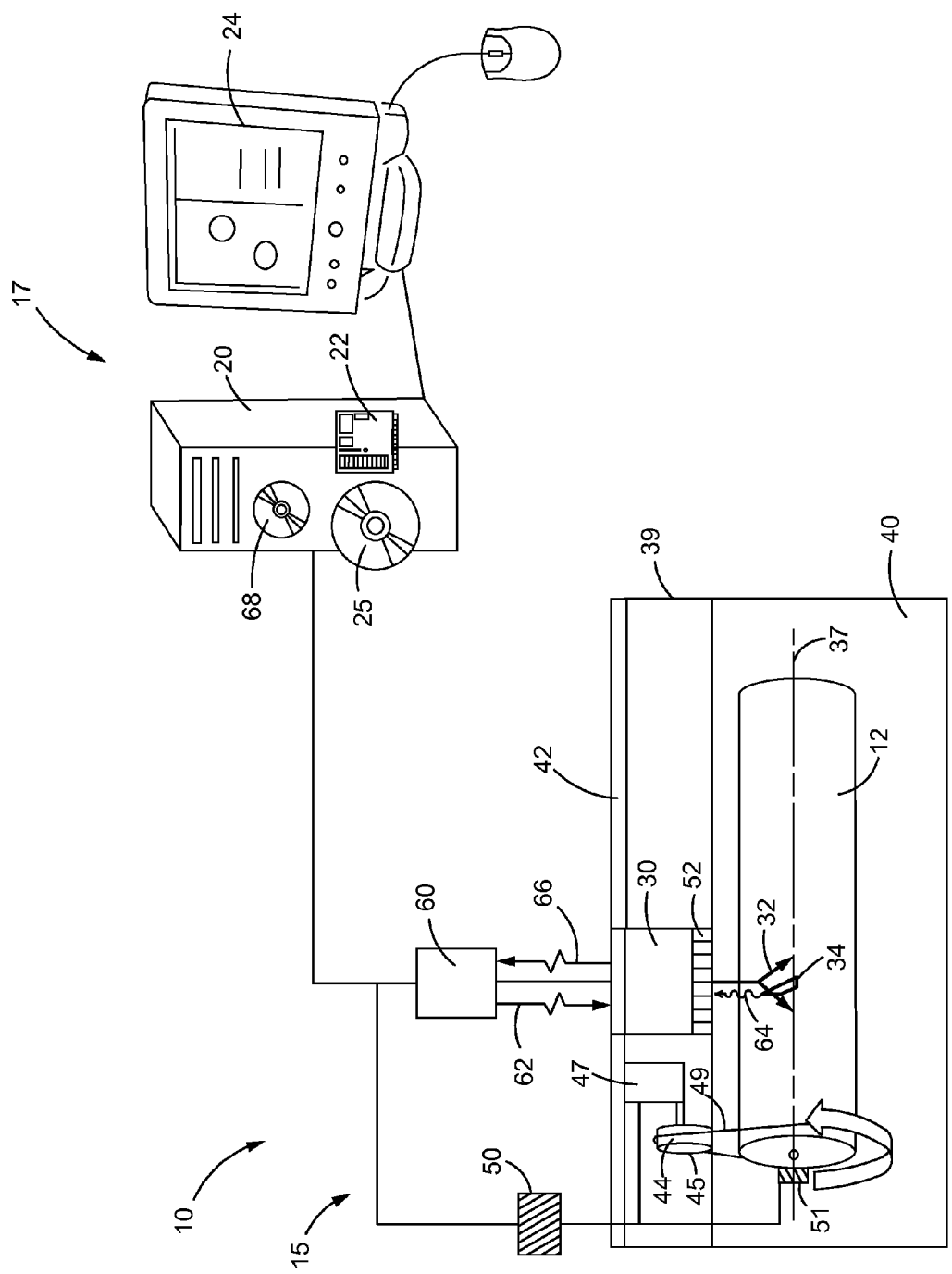
FIG. 1 is a schematic representation of a phased array system, including a data evaluation software, for the non-destructive inspection of a cylindrical billet in accordance with the present disclosure.

Referring now to the drawings, and with specific reference to FIG. 1, a phased array system 10 for the non-destructive inspection of a cylindrical billet 12 is shown. The phased array system 10 may be employed for evaluating the billet 12 for structural defects prior to its incorporation into an aircraft engine or other relevant structure, machine, or engine. Alternatively, the phased array system 10 may be employed for the non-destructive testing of other objects and shapes as well. The billet 12 may be an engine disk precursor designed for incorporation into an aircraft engine and may be made of titanium or another metallic composition. The billet 12 may have a length in the range of ten to twenty feet and a diameter in the range of six to fifteen inches. Those of ordinary skill in the art will understand that, depending on varying circumstances, the billet 12 may have other compositions, other dimensions, and other industrial applications.

Phased array system 10 may include instrumentation 15 coupled to a computer system 17, as shown. The instrumentation 15 may perform the function of acquiring structural defect data from the billet 12 and the computer system 17 may collect, evaluate, process, display, and store the defect data acquired by the instrumentation 15. The computer system 17 may have a computer unit 20, including a central processing unit 22, and a display unit 24, as shown. The computer unit 20 may include data evaluation software 25 having programmed instructions for carrying out the collection, evaluation, processing, and display of structural defect data acquired by the instrumentation 15, as further described in detail below. The central processing unit 22 may execute the instructions of data evaluation software 25.

Figure 3:
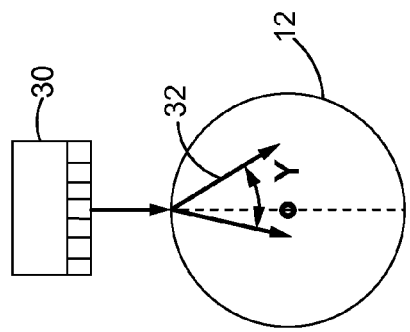
FIG. 3 is a cross-sectional view through the section 2-2 of FIG. 2 illustrating beam sweeping along a transverse axis of the billet in accordance with the present disclosure.
Figure 2:
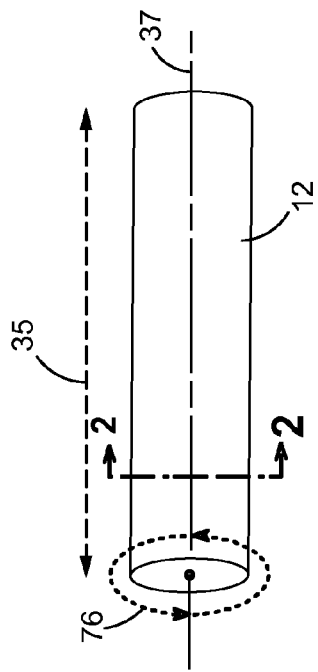
FIG. 2 is a perspective view of the cylindrical billet in accordance with the present disclosure.

The instrumentation 15 may have a probe unit 30 which may be used to probe the billet 12 with an ultrasonic beam 32 in order to inspect the billet for any structural defects 34. The structural defects 34 may be in the form of internal cracks, voids, holes, inclusions, discontinuities, and/or other structural imperfections. The probe unit 30 may be translated along a longitudinal axis 35 (see FIG. 2) of the billet 12, while the billet 12 is rotated about its central axis 37 for inspection of the billet volume of interest. Furthermore, the ultrasonic beam 32 may be swept through a sweeping angle Y by beam sweeping in order to ensure that no central region of the billet 12 is left uninspected (see FIG. 3 and further details below). Alternatively, the probe unit 30 may transmit the ultrasonic beam 32 through the billet 12 without sweeping through an angle.

Referring still to FIG. 1, the instrumentation 15 may have an immersion tank 39 for housing the billet 12 during inspection. The immersion tank 39 may be filled with a fluid 40 which may be water or another suitable fluid capable of transmitting ultrasonic waves. The billet 12 may be submerged in the fluid 40 for the duration of the phased array inspection, with the probe unit 30 being separated from the billet 12 by the fluid 40, as shown. Alternatively, if immersion testing is not employed, the probe unit 30 may be in direct contact with the surface of the billet 12.

The probe unit 30 may be slidably mounted on a track 42 such that the probe unit 30 may be translated along the longitudinal axis 35 of the billet 12. Alternatively, another mechanical instrument may be employed to translate the probe unit 30 along the longitudinal axis 35. In addition, the instrumentation 15 may have one or more billet rotators 44 for rotating billet 12 about its central axis 37. The billet rotator 44 may include a pulley 45 that may be activated by a motor 47 as well as a belt 49 to engage and rotate the billet 12. Alternatively, the billet 12 may be rotated by another equivalent mechanical instrument. The instrumentation 15 may also have a controller 50 for controlling, through the operation of the motor 47, both the translation of the probe unit 30 along the longitudinal axis 35 of the billet as well as the rate of rotation of the billet 12 about its central axis 37. In this way, the controller 50 may further act to coordinate the movement of the probe unit 30 with the rotation of the billet 12. In that regard, the billet 12 may have an encoder 51 to allow monitoring of billet rotation by the controller 50, with the controller 50 being in electrical communication with the billet encoder 51, the probe unit 30, the motor 47, and the computer system 17, to effect such coordination.

The probe unit 30 may also contain a plurality of individual transducer elements 52, as shown, which are responsible for pulsing ultrasonic waves that constructively or destructively combine to generate the ultrasonic beam 32. Each of the transducer elements 52 may be comprised of a material, such as a piezoelectric material, that is capable of converting electrical signals into ultrasonic waves and vice versa. While any number of transducer elements may be possible, the probe unit 30 may have between about 16 and about 256 individual transducer elements. Transducer elements 52 may be arranged on probe unit 30 in such a way to permit beam steering capabilities as will be readily understood by those of ordinary skill in the art.

Figure 4:
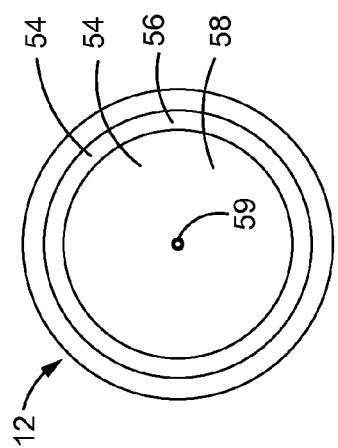
FIG. 4 is a cross-sectional view through the section 2-2 of FIG. 2 illustrating the near zone and the deep zone of the billet as inspected by the phased array system in accordance with the present disclosure.

Referring now to FIG. 4, it can be seen that the probe unit 30 may separately and simultaneously inspect two cylindrical zones 54 of the billet 12. Specifically, the probe unit 30 may simultaneously and separately inspect a near zone 56 and a deep zone 58 of the billet 12. The near zone 56 may be a cylindrical shell starting about 0.2 inches deep into the billet 12 and ending about one inch deep into the billet 12, while the deep zone 58 may be a cylindrical volume starting about one inch deep into the billet and penetrate to the billet center 59, as shown. The volumes and dimensions for the cylindrical zones 54 are of course exemplary, as other volumes and dimensions are possible. The inspection of the two cylindrical zones 54 of the billet 12 may be achieved using different transducer elements 52 located on two different segments of probe unit 30 as will be understood by the skilled artisan. However, the number and location of inspection zones may vary depending on the application in question, as well as other factors.

Referring back to FIG. 1, the probe unit 30 may be electrically connected to a pulser/receiver unit 60, as shown. The pulser/receiver unit 60 may also be referred to as the phased array instrument. The transducer elements 52 may convert electrical pulses 62 received from the pulser/receiver unit 60 into ultrasonic sound waves that form the ultrasonic beam 32. Furthermore, the transducer elements 52 may convert reflected ultrasonic echo signals 64 arising from any defects 34 into echo electronic signals 66 that are sent back to the pulser/receiver unit 60, as shown. Detection of any defects 34 may be carried out in this way for both the near zone 56 and the deep zone 58 of the billet 12.

To govern the entire operation, the computer 20 may be in electrical communication with the pulser/receiver unit 60 as well. As best shown in FIG. 1, the data evaluation software 25 may provide a set of instructions for the central processing unit 22 to perform the functions of collecting the echo signals 66 from the pulser/receiver unit 60, evaluating the echo signals 66, and processing the echo signals for display to an operator on the display unit 24 (see further details below). The computer 20 may further include a focal law software 68 which may be a set of instructions for the central processing unit 22 to perform the function of establishing the programmed time delays for firing each of the transducer elements 52 required to produce the desired ultrasonic beam 32. The focal law calculator 68 may also provide a set of instructions for the central processing unit 22 to send the programmed time delay command to the pulser/receiver unit 60 to initiate the firing of the transducer elements 52 according to the established program time delays. Alternatively, the focal law calculator 68 may be combined with the data evaluation software 25 as a single software program providing the computer executable instructions of each.

In operation, the operator may input the region of the billet 12 that is to be inspected for defects and initiate the data acquisition at the computer display 24. Phased array ultrasonic inspection of billet 12 may then proceed in an automated fashion. First, the central processing unit 22 may perform the function of establishing the specific time delays for pulsing the firing of the transducer elements 52 required to produce the desired ultrasonic beam and/or the desired beam sweeping effects according to the instructions of the focal law calculator 68. The central processing unit 22 may also send the pulsing sequence command to the pulser/receiver unit 60. In turn, the pulser/receiver 60 may then send electronic pulses 62 to the probe unit 30 according to the pulsing sequence command and thereby initiate the firing of the transducer elements 52 to produce the desired ultrasonic beam 32. The produced ultrasonic beam 32 may be sent through the billet 12 along its transverse axis and may sweep through an angle Y (see FIG. 3). The volume of interest of the billet 12, including the near zone 56 and the deep zone 58, is probed with the ultrasonic beam 32 as the billet rotates about its central axis 37 and the probe unit 30 translates along the longitudinal axis 35 of the billet.

Figure 5:
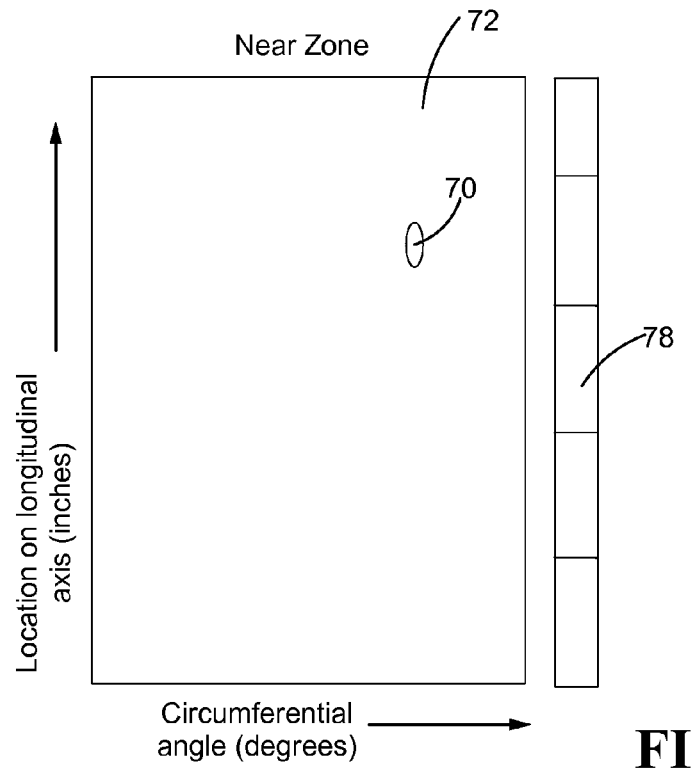
FIG. 5 is a representative c-scan image of the near zone of the billet in accordance with the present disclosure.
Figure 6:
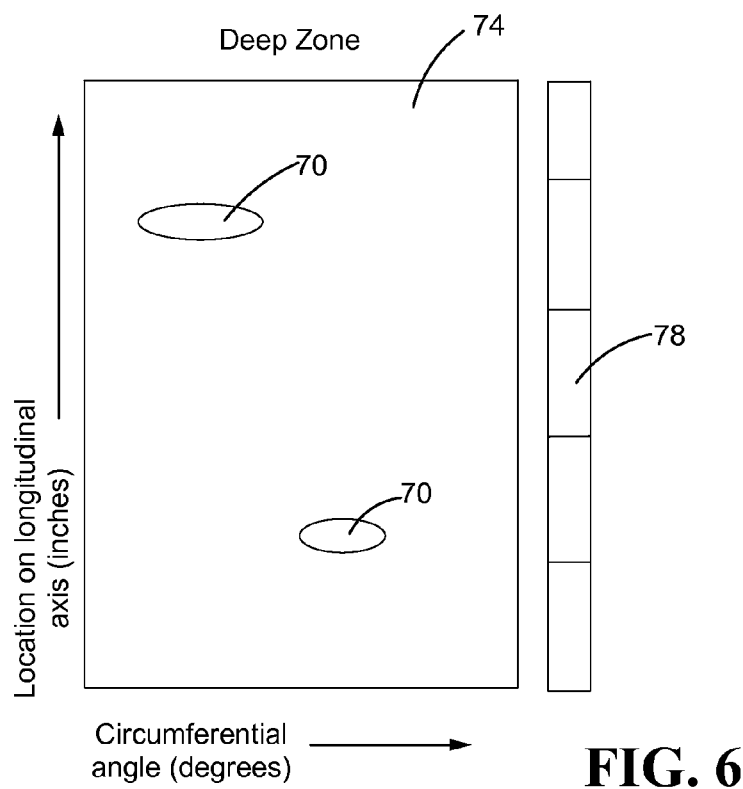
FIG. 6 is a representative c-scan image of the deep zone of the billet in accordance with the present disclosure.

If a defect 34 is encountered during the inspection, an echo signal 64 may be reflected back to the probe unit 30, as shown. The echo signals 64 resulting from background noise may also be reflected to the probe unit 30 in this way. After receiving any reflected echo signals 64, the transducer elements 52 may subsequently transmit a corresponding echo electronic signal 66 to the pulser/receiver unit 60, as shown. The processing unit 22 may then execute the functions of collecting the reflected echo signals 66 from the pulser/receiver unit 60, correlating the collected echo signals with a position on the billet 12 based on positional information provided by the controller 50, and determining an amplitude for each of the collected echo signals. The processing unit 22 may further present the echo information as indications 70 to the operator on the display unit 24 as two separate c-scan images corresponding to data obtained from the near zone 56 and the deep zone 58, as depicted by the representative c-scan data plots 72 and 74 shown in FIG. 5 and FIG. 6, respectively. It should be understood that the c-scan data plots 72 and 74 are of course, exemplary as the billet flaw patterns may vary substantially depending on the quality of the billet.

The c-scan data plots 72 and 74 of the near zone 56 and the deep zone 58 may provide flattened two-dimensional visual images of the billet 12, with the location on the longitudinal axis 35 shown on one axis and the circumferential angle 76 shown on the other axis. The echo signals 66 corresponding to any defects 34 or noise may be observable to the operator as indications 70 having amplitudes which correlate to the sizes of the defects 34 and positions directly correlating to their positions in the billet 12. The magnitude of the amplitudes for each indication 70 displayed in the c-scan plots 72 and 74 may be indicated by their spot sizes as well as by their color using a color code bar 78.

Figure 7:
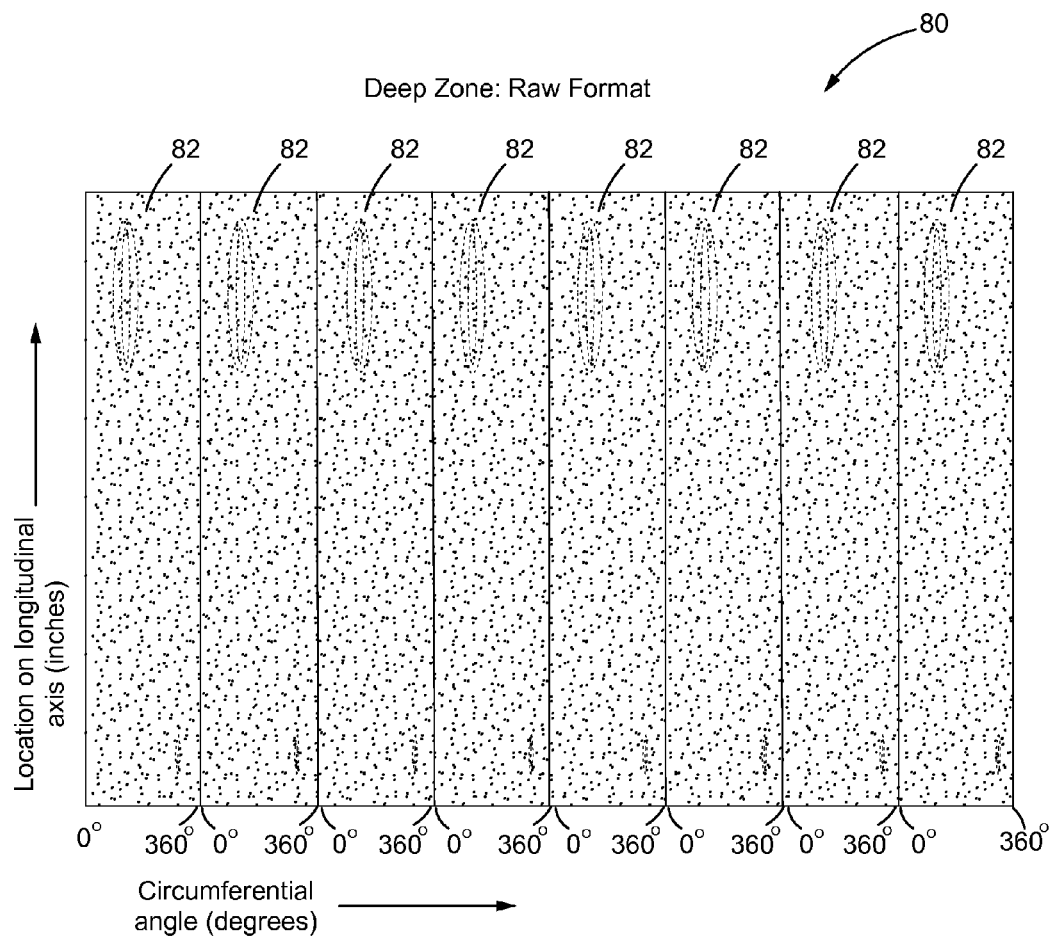
FIG. 7 is a representative raw c-scan image of the deep zone of the billet obtained by beam sweeping in accordance with the present disclosure.
Figure 8:
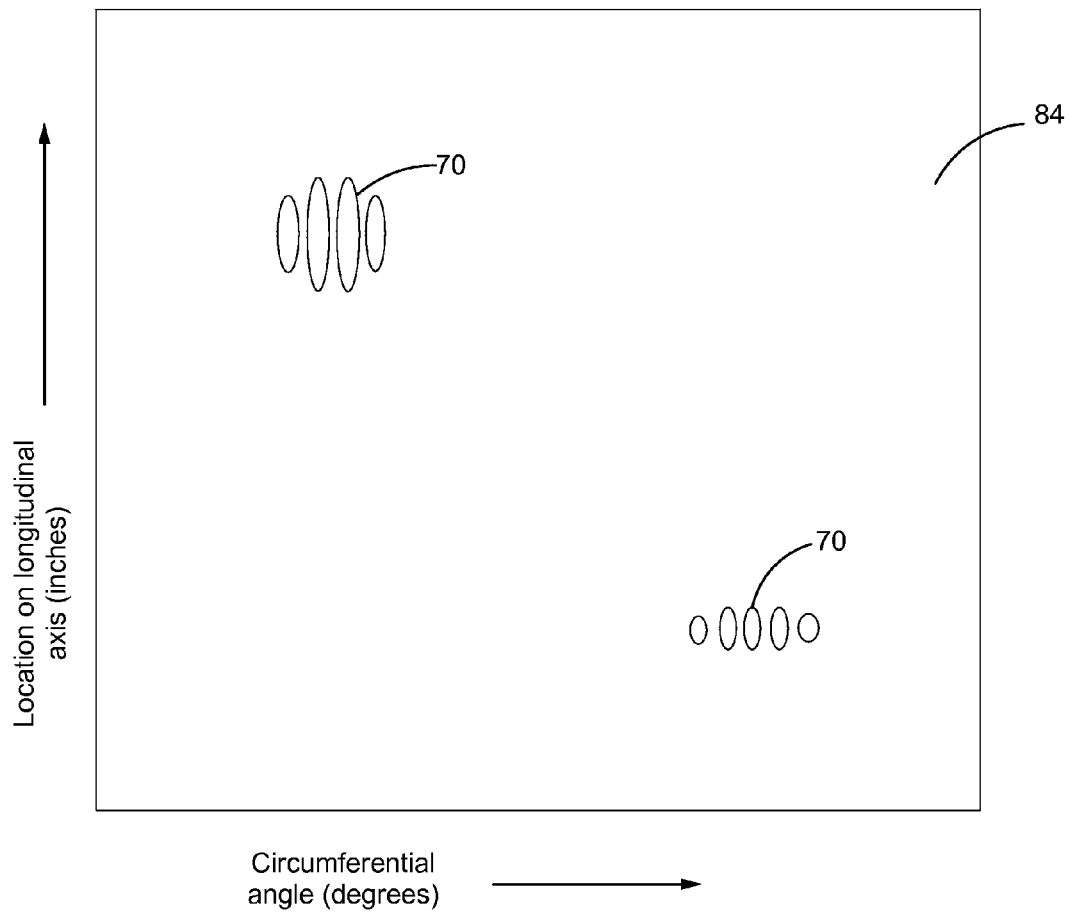
FIG. 8 is a representative merged c-scan image of the deep zone of the billet obtained by beam sweeping in accordance with the present disclosure.

Referring now to FIG. 7, a representative raw c-scan data plot 80 of the deep zone 58 of the billet 12 obtained by beam sweeping is depicted. A similar raw c-scan data plot may be obtained for the near zone 56 (not shown). If beam sweeping is employed, the billet 12 may complete a full 360° rotation about its central axis as the ultrasonic beam 32 sweeps through an angular increment of angle Y and a separate incremental c-scan plot 82 may be obtained for each angular increment of the beam sweep through the angle Y. Accordingly, the data evaluation software 25 may instruct the processing unit 22 to display the raw c-scan data plot 80 having aligned incremental c-scan plots 82 representing each angular increment of the beam sweep, as shown in FIG. 7. Each individual incremental c-scan plot 82 may show an image for a full 360° rotation along the circumferential angle 76. The number of aligned incremental c-scan plots 82 in the raw c-scan plot may vary depending on the number of angular increments in the beam sweep. Furthermore, since the transducer elements 52 may be fired a limited number of times while the beam 32 passes through the angular increment, the incremental c-scan plots 82 are obtained at less than full spatial resolution, as shown. In order to provide a c-scan data plot having full resolution, the data evaluation software 25 may instruct the processing unit 22 to merge the incremental c-scan plots 82 to provide a merged c-scan data plot 84 having full resolution, as shown in FIG. 8. As shown in the figure, each indication 70 in the merged c-scan plot 84 may consist of multiple signals and this may result from beam sweeping on and off of the defect 34 during scanning of the deep zone 58. Following data merging, the data evaluation software 25 may instruct the processing unit 22 to permit the operator to view echo data obtained by beam sweeping in either the raw form (FIG. 7) or merged form (FIG. 8) at the display unit 24 for both the near zone 56 and the deep zone 58. Furthermore, the data evaluation software 25 may instruct the processing unit 22 to permit the operator to switch back and forth between c-scan viewing in the raw and merged formats at the computer display unit 24.

Figure 9:
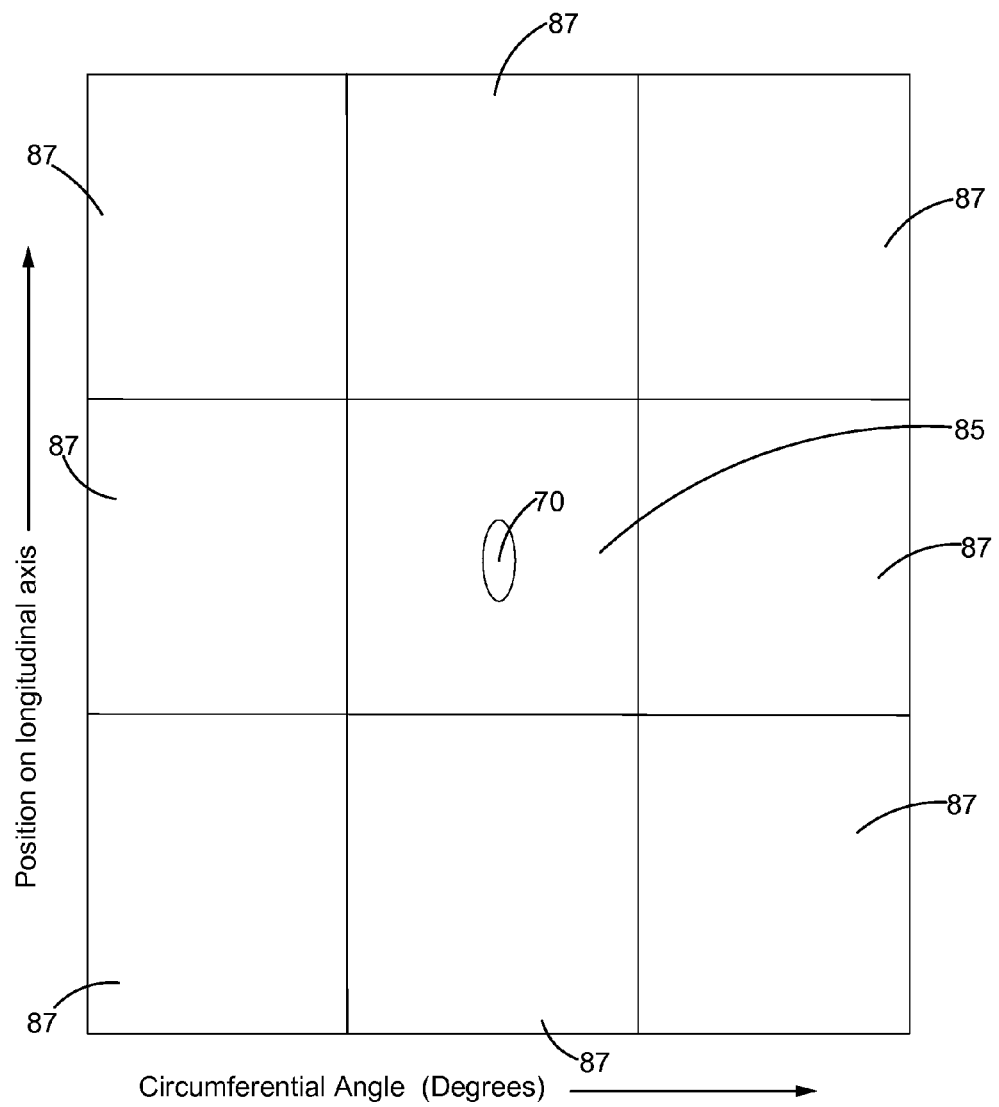
FIG. 9 is the evaluation of region-of-interest (ROI) boxes in a c-scan image as dictated by the data evaluation software in accordance with the present disclosure.

As best shown in FIG. 9, the processing unit 22 may evaluate the amplitudes of indications 70 in region-of-interest boxes (ROI) 85 of the c-scan plots 72 and 74 (or any merged c-scan plot 84 if beam sweeping is employed) according to the instructions of the data evaluation software 25. Specifically, the data evaluation software 25 may instruct the processing unit 22 to evaluate the amplitudes of the indication(s) 70 in the ROI boxes 85 relative to surrounding boxes 87, as shown, in order to determine the signal-to-noise (S/N) ratio of each indication 70. The number of surrounding boxes 87 used in the signal-to-noise evaluation may be eight, as shown, but other numbers of surrounding boxes 87 may also apply. The ROI boxes 85 may represent a two-dimension region of the billet 12 characterized by a specified length along the longitudinal axis 35 and a specified number of degrees along the circumferential direction 76, as shown in FIG. 9. For example, the ROI boxes 85 may be between about one-half of an inch to about six inches long along the longitudinal axis 35 and between about five and thirty degrees wide along the circumferential direction 76. The surrounding boxes 87 and the ROI boxes 85 may have identical dimensions, as shown. However, one of ordinary skill in the art will understand that the specific dimensions of the ROI boxes 85, the specific dimensions of the surrounding boxes 87, and the number of surrounding boxes 87 used for the S/N ratio calculation may vary considerably depending on a number of factors.

According to the instructions of the data evaluation software 25, the processing unit 22 may compute the S/N ratio of any indication(s) 70 found in a ROI box 85 according to equation (1) below, where A may be the amplitude of the indication 70 of interest in the ROI box 85, B may be the average of the average noise amplitude found in the eight surrounding boxes 87, and C may be the average of the highest signal amplitudes (peaks) found in the eight surrounding boxes 87. However, if the average noise in a surrounding box 87 is above a designated threshold value, the processing unit 22 may eliminate the surrounding box 87 from the calculation in equation (1). The processing unit 22 may eliminate up to three surrounding boxes 87 in this way. The processing unit 22 may evaluate a series of ROI boxes 85 according to equation (1) such that the S/N ratios of all indications 70 existing in the volume of near zone 56 and deep zone 58 of billet 12 may be calculated.

$$S/N = (A-B)/(C-B) \qquad (1)$$

The data evaluation software 25 may further instruct computer processing unit 22 to classify any indications 70 as "reportable", "rejectable", or insignificant depending on their calculated S/N ratios and and/or their signal amplitudes. Indications 70 having a S/N ratio above a pre-defined signal-to-noise threshold and/or an amplitude equal to or above a pre-defined amplitude threshold may be classified as "rejectable". The pre-defined signal-to-noise threshold may be 2.5 and the pre-defined amplitude threshold may be a percent amplitude of about 70% based on calibration relative to a known standard made prior to the inspection of the billet 12, but other pre-defined signal-to-noise thresholds and pre-defined amplitude thresholds may apply. Indications 70 having signal amplitudes falling within a pre-defined range of signal amplitudes may be classified as "reportable". The pre-defined range of signal amplitudes may be percent amplitudes between about 40% and about 70% based on calibration relative to a known standard made prior to the inspection of the billet 12, but other pre-defined ranges of amplitudes may apply. Indications having signal-to-noise ratios below the pre-defined range of signal amplitudes may be classified as insignificant.

The detection of one or more rejectable indications may indicate that the region of the billet carrying the defect 34 may require excision from the billet 12. The detection of a reportable indication may indicate that a rejectable defect may exist in the billet 12 but may have missed full detection during the automated phased array measurement due to system vibrations and/or the non-continuous firing of the transducer elements 52. Any indication 70 flagged as a reportable indication may be investigated further by manual re-inspection in order to confirm that the reportable condition is not a rejectable condition that missed full detection in the automated phased array measurement (see further details below).

Referring now to FIG. 10, a representative output data table 90 in accordance with the present disclosure is depicted. As instructed by the data evaluation software 25, the processing unit 22 may display output data tables 90 reporting on any reportable and rejectable indications 70 found in both the near zone 56 and the deep zone 58 of the billet 12. The processing unit 22 may display the output data tables 90 at the computer display unit 24 for viewing and analysis by the operator. As shown in FIG. 10, the output data tables 90 may list any rejectable and reportable indications 70, their amplitudes, their axial and angular locations along the longitudinal axis 35 and the circumferential angle 76, respectively, their S/N ratios, and their status (classification) as "reportable" or "rejectable" (insignificant indications may not listed). In addition, the output data tables 90 may further list average noise amplitudes and average peak noise amplitudes for the surrounding boxes 87, as shown. The processing unit 22 may display separate output data tables 90 for the near zone 56 and the deep zone 58 or it may display both sets of data in a single output data table. Furthermore, the processing unit 22 may transfer the data of output data tables 90 for display as an output data spreadsheet 91 (see FIG. 11) at a user interface provided by another data analysis program such as, but not limited to, Microsoft Excel®, where data entries may be further manipulated, stored, and processed by the operator (see further details below).

Depending on the quality and structural integrity of the billet 12, output data tables 90 may have both rejectable and reportable indications, only rejectable indications, or only reportable indications. If a reportable indication is displayed to the operator, the operator may then manually re-inspect the reportable indication by placing the probe unit 30 on the corresponding axial and angular position of the billet 12 and manually firing the transducer elements 52 to transmit an ultrasonic beam through the relevant region. In contrast to the automated phased array measurement where significant vibrations may exist due to billet rotation and probe unit movement, the probe unit 30 is held steady during the manual measurement such that the detectability of any reflected echo signal(s) 66 may be significantly improved compared with the automated measurement. Moreover, the manual phased array measurement may involve continuous firing of the transducer elements 52, thereby further improving the detectability of any reflected echo signal(s) 66.

After manual re-inspection, a new indication 70 corresponding to the echo signal 66 of the re-inspected billet region is displayed to the operator as an A-scan image at the computer display 24 (not shown). The operator may then input the corrected amplitude of the indication 70 into the output data spreadsheet 91 (see 'corrected amplitude' column), preferably at a user interface provided by Microsoft Excel® or another data analysis program. Using the average noise and average peak noise values determined in the automated measurement, a corrected S/N ratio may be computed in the data analysis program according to equation (1) (see 'corrected S/N' column in FIG. 10). If the corrected amplitude is equal to or above the pre-defined amplitude threshold and/or the corrected S/N ratio is above the pre-defined signal-to-noise threshold, the re-evaluated indication may be re-classified as "rejectable" and the corrected status may be displayed to the operator in the output data spreadsheet (see 'corrected status' column in FIG. 11).

Figure 12:
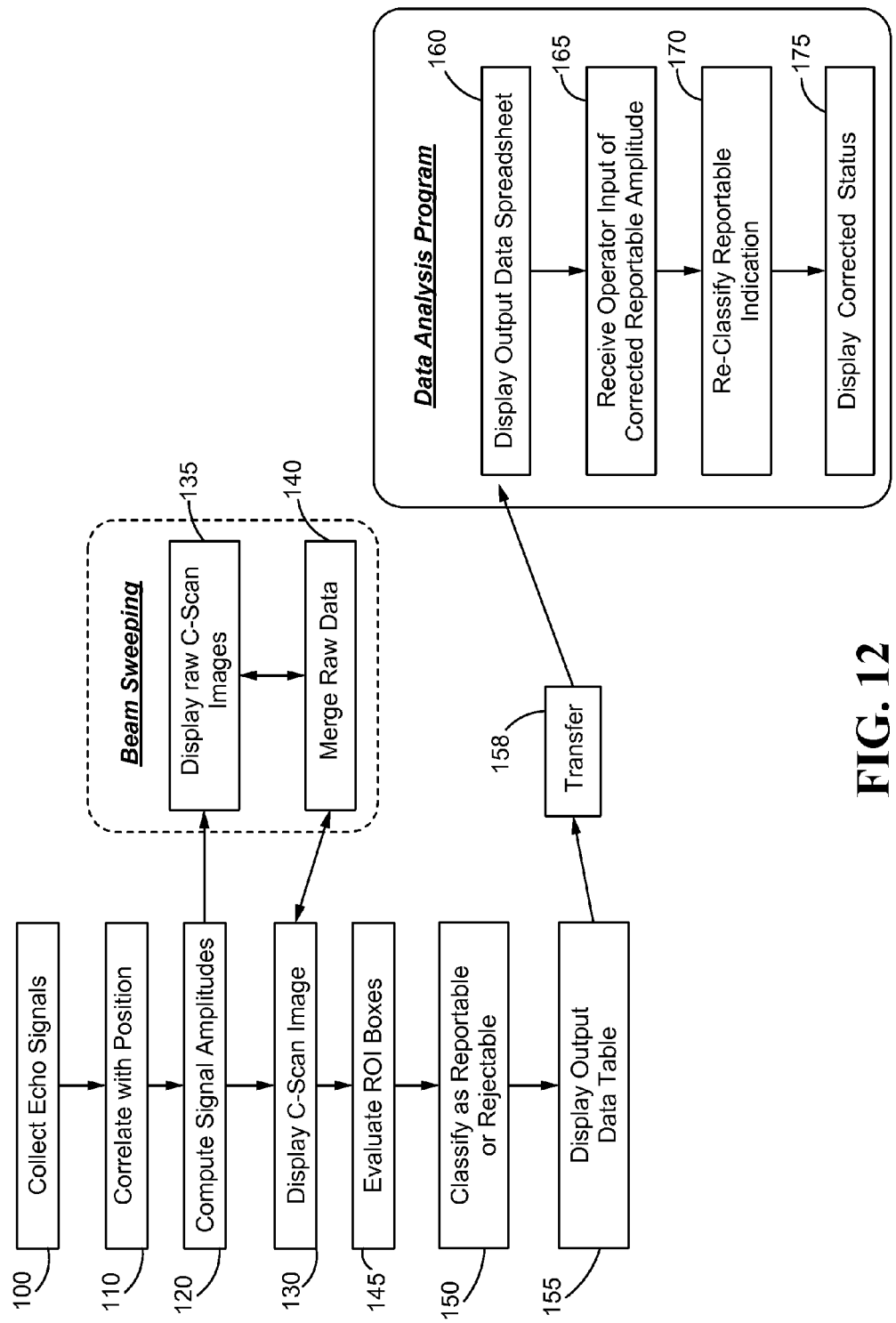
FIG. 12 is a flowchart depicting a sample sequence of steps involved in phased array echo data evaluation as dictated by the data evaluation software in accordance with the present disclosure.

In operation, the method of the present disclosure may be practiced in accordance with the flowchart of FIG. 12 which illustrates a sample sequence of steps involved in phased array echo data evaluation carried out by the processing unit 22 as dictated by the data evaluation software 25. Starting with a block 100, the processing unit 22 may interface with the pulser/receiver unit 60 to collect any return echo signals 66 resulting from defects 34 or noise in the near zone 56 and the deep zone 58 of the billet 12. The processing unit 22 may further correlate the collected return echo signals 66 with a position along the longitudinal axis 35 and the circumferential angle 76 based on positional information provided by the controller 50 according to a block 110. According to a block 120, the processing unit 22 may then determine the amplitudes of any return echo signals 66 based upon calibration relative to a known standard made prior to the billet inspection experiment. If beam sweeping is not employed for the phased array measurement, the processing unit 22 may directly display the collected echo signal information as c-scan data plots, such as the representative c-scan plots 72 and 74 shown in FIGS. 5-6, according to a block 130. During the block 130, the processing unit 22 may display separate c-scan data plots for both the near zone 56 and the deep zone 58 at the display unit 24.

If beam sweeping is employed for the phased array measurement, the processing unit 22 may display low resolution raw c-scan data plots, such as the representative raw c-scan plot 80 shown in FIG. 7, according to a block 135. The processing unit 22 may display two separate raw c-scan data plots for both the near zone 56 and the deep zone 58 at display unit 24 during the block 135. The processing unit 22 may also merge the raw c-scan data plots to provide a high resolution merged c-scan data plot for each inspected zone 54, such as the representative merged c-scan data plot 84 shown in FIG. 8, according to a block 140. Once merged, the processing unit 22 may then display the high resolution merged c-scan data plots at the display unit 24 according to the block 130. Furthermore, as shown in FIG. 11, the processing unit 22 may be capable of switching the c-scan display back and forth between the raw and merged formats, according to the operator's selection.

In a next block 145, the processing unit 22 may determine the S/N ratios of any indications 70 found in the ROI Boxes 85 of the c-scan data plots (or merged c-scan data plots) displayed during the block 130 using equation (1) (see FIG. 9). The processing unit 22 may evaluate the S/N ratios of all indications 70 found within the entire volume of the near zone 56 and the deep zone 58 during the block 145. According to a block 150, the processing unit 22 may classify any indication(s) 70 as "reportable", "rejectable", or insignificant based on their signal amplitudes and/or S/N ratios computed during the blocks 120 and 145, respectively.

According to a block 155, the processing unit 22 may display the amplitudes of any reportable or rejectable indications 70, their S/N ratios, their classification as "reportable" or "rejectable", as well as the average noise and average peak noise found in the surrounding boxes 87 as an output data table 90 at the display unit 24 for viewing by an operator at the display unit 24 (see FIG. 10). The processing unit 22 may further transfer the data of the output data table 90 to another data analysis program, such as Microsoft Excel®, and the table information may then be displayed as output data spreadsheets 91 at an interface provided by the data analysis program, according to a block 158 and a block 160, respectively.

Once the foregoing is performed, the processing unit 22 may then receive manually measured corrected amplitudes for any reportable indications as depicted by a block 165. The receipt of the manually measured corrected signal amplitudes may occur when the operator enters the corrected amplitude into the spreadsheet 91 (see FIG. 11). The corrected amplitudes are subsequently re-classified as reportable or rejectable and the corrected status of the indication may be displayed in the spreadsheet 91 according to a block 170 and a block 175, respectively. Blocks 165, 170, and 175 may be performed within the constructs display interfaces provided by another data analysis program, such as Microsoft Excel®, as shown. Alternatively, blocks 165, 170, and 175 may be performed within the constructs of display interfaces provided by data evaluation software 25.

INDUSTRIAL APPLICABILITY

From the foregoing, it can be seen that the present disclosure may find industrial applicability in many situations, including, but not limited to, inspection of billets. More specifically, the present disclosure describes a computer-implemented method for evaluating and processing ultrasonic phased-array echo data signals arising from structural defects in billets. The computer-implemented method overcomes some of the limitations associated with evaluating echo signals by phased array measurements, such as background noise and false detections. Moreover, the computer-implemented method improves the evaluation of echo signal data obtained during automated phased array measurements. The computer-implemented method may find wide industrial applicability in areas such as, but not limited to, quality control evaluations in the aircraft industry.

What is claimed:

1. A computer-implemented method for evaluating echo signals obtained from a phased array experiment on a billet comprising:

collecting the echo signals from a pulser/receiver unit;

correlating the echo signals with a position on a longitudinal axis and a circumferential angle of the billet;
computing an amplitude for each of the echo signals;
displaying the amplitudes as indications in a c-scan data plot at a computer display unit; and
determining a signal-to-noise ratio for each indication located in a region-of interest box relative to surrounding boxes in the c-scan data plot, the signal-to-noise ratio being determined by the equation: signal-to-noise ratio=(A−B)/(C−B), where A is the amplitude of the indication in the region-of-interest box, B is the average of the average noise in the surrounding boxes, and C is the average of the highest signal amplitudes in the surrounding boxes.

2. The computer-implemented method according to claim 1, wherein determining the signal-to-noise ratio for each indication located in a region-of-interest box is performed for the entire volume of a first cylindrical zone of the billet.

3. The computer-implemented method according to claim 2, wherein determining the signal-to-noise ratio for each indication located in a region-of-interest box is further performed for the entire volume of a second cylindrical zone of the billet.

4. The computer-implemented method according to claim 3, wherein determining a signal-to-noise ratio for each indication located in a region-of interest box is determined relative to eight surrounding boxes.

5. The computer-implemented method of claim 3, further comprising classifying each indication as reportable, rejectable, or insignificant based on the signal-to-noise ratio and the amplitude of each indication.

6. The computer-implemented method of claim 5, wherein each indication having an amplitude falling within a pre-defined range of signal amplitudes is classified as reportable.

7. The computer-implemented method of claim 5, wherein each indication having an amplitude equal to or above a pre-defined amplitude threshold is classified as rejectable.

8. The computer-implemented method of claim 5, wherein each indication having a signal-to-noise ratio above than a pre-defined signal-to-noise threshold is classified as rejectable.

9. The computer-implemented method of claim 5, further comprising displaying an output data table at the computer display unit, the output data table listing the amplitudes of reportable indications and rejectable indications, the position of the reportable indications and the rejectable indications on the longitudinal axis and the circumferential angle, the signal-to noise ratios of the reportable indications and the rejectable indications, and the classification of the reportable indications and the rejectable indications as reportable or rejectable.

10. The computer-implemented method of claim 9, further comprising receiving operator input of a manually measured amplitude of a reportable indication.

11. The computer-implemented method of claim 10, further comprising re-classifying the manually measured amplitude as reportable, rejectable, or insignificant.

12. The computer-implemented method of claim 11, wherein the computer-implemented method is performed for both a first cylindrical zone and a second cylindrical zone of the billet.

13. A computer-implemented method for evaluating echo signals obtained from a phased array experiment on a billet, the phased array experiment being performed by transmitting an ultrasonic beam through the billet, the ultrasonic beam being swept through a sweeping angle, said method comprising:
collecting the echo signals from a pulser/receiver unit;
correlating the echo signals with a position on a longitudinal axis and a circumferential angle of the billet;
computing an amplitude for each of the echo signals;
displaying the amplitudes as indications in a raw c-scan data plot at a computer display unit, the raw c-scan data plot having a series of aligned low resolution incremental c-scan plots, the incremental c-scan plots each corresponding to an angular increment of the sweeping angle;
merging the incremental c-scan plots to provide a high-resolution c-scan plot; and
displaying the high-resolution c-scan plot at the computer display unit.

14. The computer-implemented method of claim 13, further comprising determining a signal-to-noise ratio for each indication located in a region-of-interest box relative to surrounding boxes in the high-resolution c-scan data plot, the signal-to-noise ratio being determined by the equation: signal-to-noise=(A−B)/(C−B), where A is the echo signal amplitude in the region-of-interest box, B is the average of the average noise in the surrounding boxes, and Cis the average of the highest signal amplitudes in the surrounding boxes.

15. The computer-implemented method of claim 14, wherein determining the signal-to-noise ratio of each indication located in a region-of-interest box is performed for the entire volume of a first cylindrical zone of the billet.

16. The computer-implemented method of claim 15, wherein determining the signal-to-noise ratio of each indication located in a region-of-interest box is further performed for the entire volume of a second cylindrical zone of the billet.

17. The computer-implemented method of claim 16, further comprising classifying each indication as reportable, rejectable, or insignificant based on the signal-to-noise ratio and the amplitude of each indication.

18. The computer-implemented method of claim 17, wherein each indication having an amplitude falling within a pre-defined range of signal amplitudes is classified as reportable.

19. The computer-implemented method of claim 17, wherein each indication having an amplitude equal to or greater than a pre-defined amplitude threshold is classified as rejectable.

20. A billet inspection system comprising an immersion tank adapted to hold a billet, a probe unit to direct an ultrasonic beam toward the billet, a pulser/receiver unit in communication with the probe unit and a central processing unit, the central processing unit being configured to perform computer executable instructions for evaluating echo signals obtained from a phased array experiment on the billet, the computer executable instructions comprising instructions for:
collecting the echo signals from the pulser/receiver unit;
correlating the echo signals with a position on a longitudinal axis and a circumferential angle of the billet;
computing an amplitude for each of the echo signals;
displaying the amplitudes as indications in a c-scan data plot at a computer display unit;
determining a signal-to-noise ratios for each indication located in a region-of interest box relative to surrounding boxes in the c-scan data plot, the signal-to-noise ratio being determined by the equation: signal-tonoise=$(A-B)/(C-B)$, where A is the echo signal amplitude in the region-of-interest box, B is the average of the average noise in the surrounding boxes, and C is the average of the highest signal amplitudes in the surrounding boxes.

\* \* \* \* \*